United States Patent
DiSilvestro et al.

(10) Patent No.: US 8,419,801 B2
(45) Date of Patent: *Apr. 16, 2013

(54) ADJUSTABLE, REMOTE-CONTROLLABLE ORTHOPAEDIC PROSTHESIS AND ASSOCIATED METHOD

(75) Inventors: Mark R. DiSilvestro, Columbia City, IN (US); Terry L. Dietz, Columbia City, IN (US); Robert S. Hastings, Warsaw, IN (US)

(73) Assignee: DePuy Synthes Products, LLC, Warsaw, IN (US)

( * ) Notice: Subject to any disclaimer, the term of this patent is extended or adjusted under 35 U.S.C. 154(b) by 234 days.

This patent is subject to a terminal disclaimer.

(21) Appl. No.: 12/491,661

(22) Filed: Jun. 25, 2009

(65) Prior Publication Data
US 2009/0259319 A1    Oct. 15, 2009

Related U.S. Application Data

(63) Continuation of application No. 11/154,339, filed on Jun. 16, 2005, now Pat. No. 7,559,951.

(60) Provisional application No. 60/615,146, filed on Sep. 30, 2004.

(51) Int. Cl.
*A61F 2/36* (2006.01)

(52) U.S. Cl.
USPC ............... 623/23.47; 623/23.16; 623/23.45

(58) Field of Classification Search ............. 623/16.11, 623/18.11, 18.12, 22.4, 23.17, 23.44–23.47; 606/61, 62, 63, 64, 68, 90, 105
See application file for complete search history.

(56) References Cited

U.S. PATENT DOCUMENTS

| | | | |
|---|---|---|---|
| 3,861,226 | A | 1/1975 | Stanley |
| 3,976,060 | A | 8/1976 | Hildebrandt et al. |
| 3,986,504 | A | 10/1976 | Avila |
| 4,024,588 | A | 5/1977 | Janssen et al. |
| 4,091,806 | A | 5/1978 | Aginsky |
| 4,157,715 | A | 6/1979 | Westerhoff |
| 4,190,044 | A | 2/1980 | Wood |
| 4,262,665 | A | 4/1981 | Roalstad et al. |
| 4,275,717 | A | 6/1981 | Bolesky |
| 4,384,373 | A | 5/1983 | Sivash |

(Continued)

FOREIGN PATENT DOCUMENTS

| | | |
|---|---|---|
| EP | 1371346 | 12/2003 |
| FR | 2425237 | 12/1979 |

(Continued)

OTHER PUBLICATIONS

"Oncology Repiphysis," http://www.wmt.com/Patients/oncology/repiphysis.asp, printed May 25, 2004, 1 pg.

(Continued)

*Primary Examiner* — Thomas J Sweet
*Assistant Examiner* — Megan Wolf
(74) *Attorney, Agent, or Firm* — Barnes & Thornburg LLP

(57) ABSTRACT

An implantable, adjustable prosthesis includes a first component which may be moved relative to a second component by use of a transcutaneous control signal. A method of operating such a prosthesis is also disclosed.

15 Claims, 4 Drawing Sheets

U.S. PATENT DOCUMENTS

| | | | |
|---|---|---|---|
| 4,453,539 A | 6/1984 | Raftopoulos et al. | |
| 4,502,160 A | 3/1985 | Moore et al. | |
| 4,520,511 A | 6/1985 | Gianezio et al. | |
| 4,681,590 A | 7/1987 | Tansey | |
| 4,892,546 A | 1/1990 | Kotz et al. | |
| 4,946,459 A | 8/1990 | Bradshaw et al. | |
| 5,057,103 A | 10/1991 | Davis | |
| 5,059,193 A | 10/1991 | Kuslich | |
| 5,062,855 A | 11/1991 | Rincoe | |
| 5,071,435 A | 12/1991 | Fuchs et al. | |
| 5,074,882 A | 12/1991 | Grammont et al. | |
| 5,100,286 A | 3/1992 | Anderson | |
| 5,102,413 A | 4/1992 | Poddar | |
| 5,108,398 A | 4/1992 | McQueen et al. | |
| 5,123,926 A | 6/1992 | Pisharodi | |
| 5,236,460 A | 8/1993 | Barber | |
| 5,263,955 A | 11/1993 | Baumgart et al. | |
| 5,326,360 A | 7/1994 | Kotz et al. | |
| 5,350,379 A | 9/1994 | Spievack | |
| 5,356,411 A | 10/1994 | Spievack | |
| 5,358,524 A | 10/1994 | Richelsoph | |
| 5,364,396 A | 11/1994 | Robinson et al. | |
| 5,415,660 A | 5/1995 | Campbell et al. | |
| 5,429,638 A | 7/1995 | Muschler et al. | |
| 5,466,261 A | 11/1995 | Richelsoph | |
| 5,505,733 A | 4/1996 | Justin et al. | |
| 5,516,335 A | 5/1996 | Kummer et al. | |
| 5,536,269 A | 7/1996 | Spievack | |
| 5,575,790 A | 11/1996 | Chen et al. | |
| 5,591,233 A | 1/1997 | Kelman et al. | |
| 5,626,579 A | 5/1997 | Muschler et al. | |
| 5,626,581 A | 5/1997 | Staehlin et al. | |
| 5,665,122 A | 9/1997 | Kambin | |
| 5,700,263 A | 12/1997 | Schendel | |
| 5,704,938 A | 1/1998 | Staehlin et al. | |
| 5,704,939 A * | 1/1998 | Justin | 606/63 |
| 5,720,746 A | 2/1998 | Soubeiran | |
| 5,827,286 A | 10/1998 | Incavo et al. | |
| 5,846,245 A | 12/1998 | McCarthy et al. | |
| 5,855,580 A | 1/1999 | Kreidler et al. | |
| 5,879,386 A | 3/1999 | Jore | |
| 5,885,283 A | 3/1999 | Gittleman | |
| 5,885,290 A | 3/1999 | Guerrero et al. | |
| 5,895,387 A | 4/1999 | Guerrero et al. | |
| 5,902,304 A | 5/1999 | Walker et al. | |
| 5,961,553 A | 10/1999 | Coty et al. | |
| 6,025,537 A | 2/2000 | Weding et al. | |
| 6,033,412 A | 3/2000 | Losken et al. | |
| 6,036,690 A | 3/2000 | De La Plaza Fernandez | |
| 6,077,265 A | 6/2000 | Werding et al. | |
| 6,106,525 A | 8/2000 | Sachse | |
| 6,113,599 A | 9/2000 | Landsberger | |
| 6,127,597 A | 10/2000 | Beyar et al. | |
| 6,176,881 B1 | 1/2001 | Schar et al. | |
| 6,187,004 B1 | 2/2001 | Fearon | |
| 6,200,317 B1 | 3/2001 | Aalsma et al. | |
| 6,224,600 B1 | 5/2001 | Protogirou | |
| 6,245,075 B1 | 6/2001 | Betz et al. | |
| 6,261,289 B1 | 7/2001 | Levy | |
| 6,277,124 B1 | 8/2001 | Haag | |
| 6,336,929 B1 | 1/2002 | Justin | |
| 6,358,283 B1 | 3/2002 | Hogfors et al. | |
| 6,368,349 B1 | 4/2002 | Wyatt et al. | |
| 6,383,185 B1 | 5/2002 | Baumgart | |
| 6,416,516 B1 | 7/2002 | Stauch et al. | |
| 6,425,923 B1 | 7/2002 | Stalcup et al. | |
| 6,447,448 B1 | 9/2002 | Ishikawa | |
| 6,447,514 B1 | 9/2002 | Stalcup et al. | |
| 6,447,515 B1 | 9/2002 | Meldrum | |
| 6,520,991 B2 | 2/2003 | Huene | |
| 6,554,833 B2 | 4/2003 | Levy et al. | |
| 6,565,576 B1 | 5/2003 | Stauch et al. | |
| 6,613,052 B1 | 9/2003 | Kinnett | |
| 6,673,079 B1 | 1/2004 | Kane | |
| 6,706,042 B2 | 3/2004 | Taylor | |
| 6,730,087 B1 | 5/2004 | Butsch | |
| 6,736,818 B2 | 5/2004 | Perren et al. | |
| 6,755,862 B2 | 6/2004 | Keynan | |
| 6,783,530 B1 | 8/2004 | Levy | |
| 6,796,984 B2 | 9/2004 | Soubeiran | |
| 6,849,076 B2 * | 2/2005 | Blunn et al. | 606/105 |
| 7,531,002 B2 * | 5/2009 | Sutton et al. | 623/17.15 |
| 2002/0115944 A1 | 8/2002 | Mendes | |
| 2003/0197481 A1 | 10/2003 | Gonzalez | |
| 2003/0204267 A1 | 10/2003 | Hazebrouck et al. | |
| 2003/0204965 A1 | 11/2003 | Hennessey | |
| 2003/0225440 A1 | 12/2003 | Cancel et al. | |
| 2004/0030395 A1 | 2/2004 | Blunn et al. | |
| 2004/0133204 A1 | 7/2004 | Davies | |
| 2004/0138663 A1 | 7/2004 | Kosashvili et al. | |
| 2004/0167625 A1 | 8/2004 | Beyar et al. | |
| 2004/0193266 A1 | 9/2004 | Meyer | |
| 2004/0193267 A1 | 9/2004 | Jones et al. | |
| 2004/0193268 A1 | 9/2004 | Hazebrouck | |
| 2005/0234555 A1 | 10/2005 | Sutton et al. | |
| 2005/0256576 A1 | 11/2005 | Moskowitz et al. | |
| 2006/0004459 A1 | 1/2006 | Hazebrouck et al. | |

FOREIGN PATENT DOCUMENTS

| | | |
|---|---|---|
| FR | 2605514 | 4/1988 |
| JP | 6086319 | 6/1985 |
| JP | 5507222 A | 10/1993 |
| JP | 9056736 A | 3/2007 |
| WO | PCT/WO9002533 | 3/1990 |
| WO | PCT/WO0044315 | 8/2000 |
| WO | PCT/WO0044319 | 8/2000 |
| WO | PCT/WO0048524 | 8/2000 |
| WO | PCT/WO0154598 | 8/2001 |

OTHER PUBLICATIONS

"Musculo-skeletal tumor orthopaedic practice, published works: special considerations for growing children," http://www.orthotumormd.com/pages/specialchildren.php, printed May 25, 2004, 10 pgs.

Walker, J. "On the cutting edge of prosthetics, Precision Machine launches new design for artificial hip," Pictorial Gazette, Jun. 24, 2003, 2 pgs.

Szabo, L., "Experiemential implant grows with young limbs; technology spares bone cancer patients painful surgeries," USA Today, Jul. 12, 2004, p. D8.

Jackson, M., "Bionic Therapy for Leg Bones," http://www.news.bbc.co.uk/2/hi/health/3917573.stm, printed Aug. 6, 2004, 3 pgs.

Sharke, P., "The machinery of life," Mechanical Engineering, Feb. 2004, 30-34.

"Drive implant eliminates follow-up surgery," http://www.design-news.com/index.asp? layout=articlePrint&articleID=CA426260, Jul. 28, 2004, 2 pgs, Jul. 28, 2004.

Dominkus, M., "Growth Predictions in Extendable Tumor Prostheses in Children," Clinical Orthopaedics and Related Research, Sep. 2001, No. 390, pp. 212-220.

Ries, et al., "Cancer incidence and survival among children and adolescents: U.S. SEER Program 1975-1995," National Cancer Institute, NIH, 1999, 99-4649.

Eckardt, et al., "Expandable endoprosthesis reconstruction in skeletally immature patients with tumors," Clinical Orthopaedics, Apr. 2000, 373, 51-61.

Verkeke, et al., "Design of a lengthening element for a modular femur endoprosthetic system," Proc. Inst. Mech. Eng., 1989, 97-102.

"Wright Medical gets FDA clearance for repiphysis technology," Memphis Business Journal, Dec. 5, 2002, 382.

Wilkins, et al, "The Phenix Expandable Prosthesis: Early American Experience," Clin. Orthop., 2001, 51-58.

Cole, et al., "The intramedullary skeletal kinetic distractor (ISKD); first clinical results of a new intramedullary nail for lengthening of the femur and tibia," Injury, Dec. 2001, 32-4, 129-139.

Neel, et al., "Modular endoprostheses for children with malignant bone tumors," Cancer Control, 2001, 8-4, 344-348.

Tudor-Locke et al., "The relationship between pedometer-determined ambulatory activity and body composition variables," Int. J. Obes., Nov. 2001, 25-11, 1571-1578.

Schmalzried, et al., "Quantitative assessment of walking activity after total hip or knee replacement," J. Bone Joint Surg. Am., Jan. 1998, 80-1, 54-59.

Gaebler, et al., "A new modular testing system for biomechanical evaulation of tibial intramedullary fixation devices, " Injury, Nov. 2001, 32-9, 708-712.

Guichett, et al., "Mechanical characterization of a totally intramedullary gradual elongation nail," Clin. Orthop., Apr. 1997, 337, 281-290.

Verkerke, et al., "First clinical experience with a non-invsively extendable endroprosthesis: a limb-saving procedure in children suffering from malignant bone tumor," Artif. Organs., May 1997, 21-5, 413-417.

Office Action dated Jun. 25, 2007, issued in U.S. Appl. No. 10/880,859, which issued as U.S. Patent No. 7,481,841.

European Search Report for European Patent Application No. 05255813.7-1269/1642550, Mar. 30, 2010, 9 pgs.

Japanese Search Report; Japanese Patent Application No. 2005-284730; Aug. 31, 2010; 3 pages.

\* cited by examiner

ADJUSTABLE, REMOTE-CONTROLLABLE ORTHOPAEDIC PROSTHESIS AND ASSOCIATED METHOD

This application is a continuation of U.S. patent application Ser. No. 11/154,339, filed on Jun. 16, 2005, and issued as U.S. Pat. No. 7,559,951 on Jul. 14, 2009, which claims priority under 35 U.S.C. §119(e) to U.S. Provisional Patent Application No. 60/615,146, filed on Sep. 30, 2004. Each of those applications is incorporated herein by reference.

FIELD OF THE DISCLOSURE

The present disclosure is related generally to orthopaedic prosthesis and methods of using the same.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a hip replacement procedure, a femoral prosthesis is implanted into the patient's femur. The femoral prosthesis typically includes an elongated stem component which is implanted into the medullary canal of the patient's femur and a spherically-shaped head which bears against the patient's acetabulum or a prosthetic replacement acetabular cup. In the case of a shoulder replacement procedure, a humeral prosthesis is implanted into the patient's humerus. The humeral prosthesis includes an elongated stem component which is implanted into the medullary canal of the patient's humerus and a spherically-shaped head which bears against the patient's glenoid or a prosthetic replacement glenoid component. In the case of a knee replacement procedure, a tibial prosthesis is implanted into the patient's tibia. The condyle surfaces of the patient's femur, or the condyle surfaces of a replacement femoral component, bear against the tibial prosthesis.

Subsequent to implantation, there is occasionally the need to adjust the prosthesis. For example, it may be necessary to adjust the prosthesis to correct a surgical error or correct for subsidence of the implant. Such adjustments necessitate one or more revision surgeries.

Moreover, each year in the United States approximately 650-700 children under the age twenty (20) are diagnosed with a malignant bone tumor. When presented with these types of cases, the surgeon can either amputate the entire limb or try to preserve it. To preserve the limb, the cancerous portion of the bone is removed. This surgery typically involves the removal of one or both of the growth plates. Because the residual bone cannot grow at the same speed as the contralateral bone, a modular endoprosthesis is often implanted. As the child grows, more surgeries are required to lengthen the device. Depending on the age and condition of the patient, the number of surgeries that the patient has to endure can be greater than twenty. Specifically, for the young patient to grow properly with a modular endoprosthesis, multiple surgeries must be completed to continually lengthen the device or replace it with a new, longer one. After the patient has reached his/her full height, it may be necessary to replace the endoprosthesis again with a permanent endoprosthesis.

SUMMARY

According to one aspect of the present disclosure, an adjustable prosthesis includes a first component which may be moved relative to a second component by use of a transcutaneous control signal.

The prosthesis may include a telescoping stem having an adjustable length.

The prosthesis may include a telescoping stem having an adjustable length and a telescoping neck having an adjustable length.

The prosthesis may include a long bone prosthesis having an adjustable length and an adjustable offset.

The prosthesis may include a tibial component.

According to another aspect of the present disclosure, there is provided a method of operating an implantable prosthesis. The method includes implanting the prosthesis and thereafter post-operatively adjusting the prosthesis.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DRAWINGS

Figure 3:
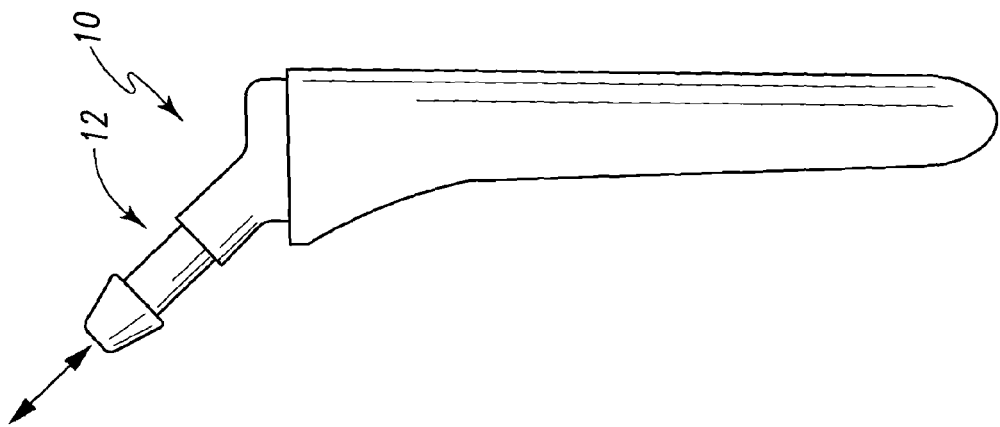
FIGS. 1-3 are diagrammatic views of an adjustable long bone prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

As will be described herein in greater detail, the remote-controllable prosthetic implants of the present disclosure allow a surgeon to post-operatively, and in some cases, transcutaneously control certain actions of the implant without the need for revision surgery. The implant may be controlled to adjust its physical shape (e.g., length, alignment, offset, thickness, radius), deliver drugs or other compounds, or correct a variety of other conditions. It should be appreciated that any such control of the implants of the present disclosure may also be performed intra-operatively if the surgeon so desires. In certain embodiments, the implants of the present disclosure may be configured with sensors or other devices which allow the implant to sense or otherwise detect certain conditions and then perform a predetermined function in response thereto.

Figure 2:
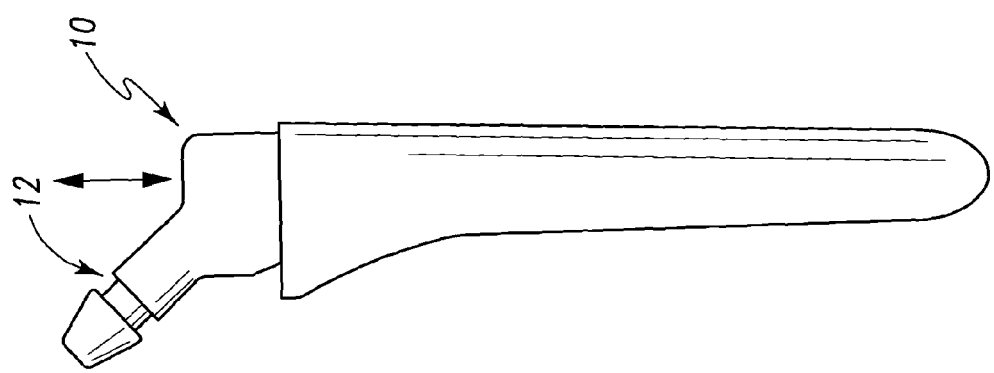
Figure 1:
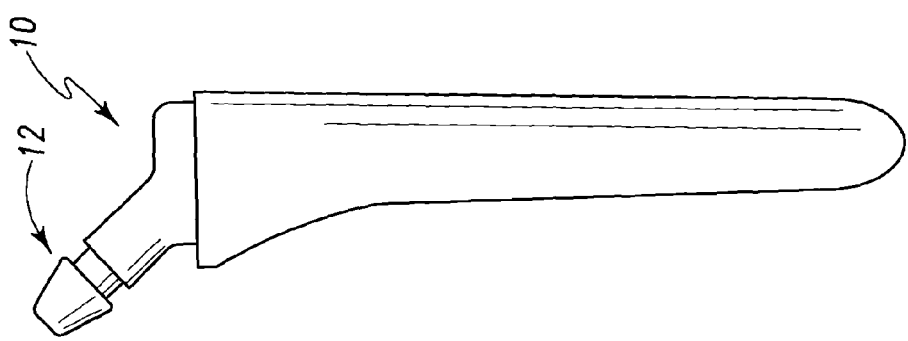

As shown in FIG. 2, the length of a long bone implant 10, such as a femoral implant, may be adjusted post-operatively to, for example, correct a surgical error or otherwise account for surgical variation such as leg length discrepancy subsequent to a hip replacement procedure. The femoral implant 10 may also be used for the post-operative correction of instability issues arising from surgical error or compromise of the patient's soft tissue (e.g., tissue stretching). In the case of a total hip replacement procedure, stability may be enhanced by moving the neck 12 of the implant 10 proximally and/or by increasing the offset to tighten the soft tissues (see FIGS. 1-3). Similarly, improvement of weak abductor function in a patient following a total hip replacement procedure may be achieved by post-operatively increasing the offset of the femoral implant 10 (see FIG. 3).

Figure 6:
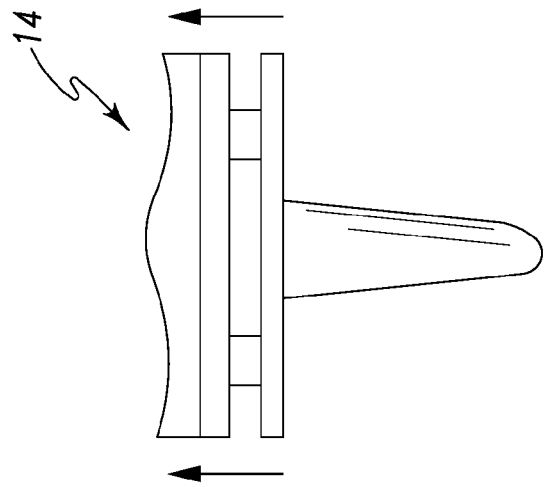
FIGS. 4-6 are diagrammatic views of an adjustable tibial prosthesis.
Figure 5:
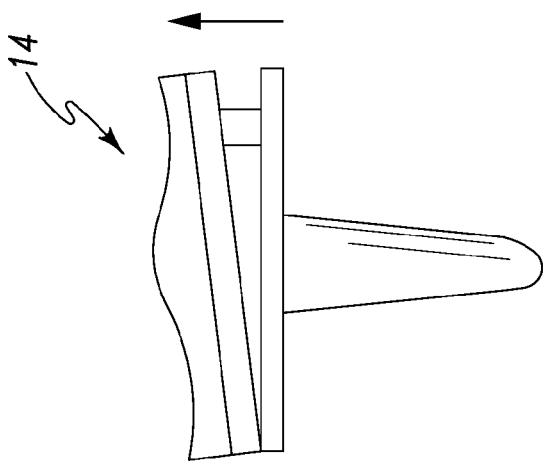
Figure 4:
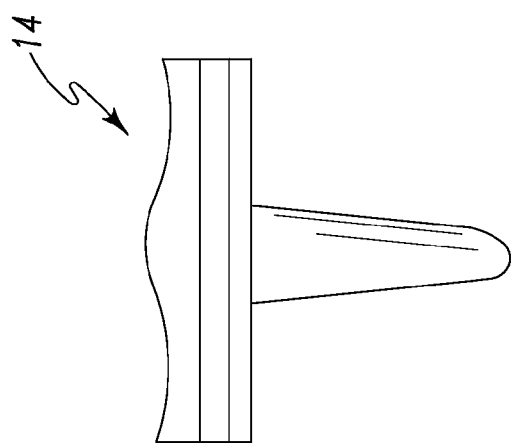

As shown in FIG. 5, a tibial implant 14 may be adjusted post-operatively to correct any tibial tray malalignment that may occur following a total knee replacement procedure. The implant 14 may also be used to post-operatively correct the occurrence of subsidence on either one side (e.g., the medial side, see FIG. 5) or both sides (e.g., both the medial and lateral sides, see FIG. 6) of the knee subsequent to a total knee replacement procedure. It should be appreciated that although medial/lateral adjustment of the tibial implant 14 is shown in FIGS. 5 and 6, such concepts may also be applied to anterior/posterior adjustment of the implant 14. The tibial implant 14 may also be used for the post-operative correction of instability issues arising from surgical error or compromise of the patient's soft tissue (e.g., tissue stretching). In the case of a total knee replacement procedure, stability may be enhanced by raising the proximal surface of the tibial tray (see FIG. 6).

The implants of the present disclosure may also be used to treat a number of different conditions by releasing a drug or other compound that is contained in the implant. For example, an antibiotic may be delivered to an infected joint from the implant. The implants may be used to release chelating agents or other compounds to capture metal ions. The implants may be used to release agents to capture or neutralize wear debris.

Remote control of the implants 10, 14 may be achieved through the use of a wireless communications link. For example, a radio-frequency (RF) or acoustic link may be used to communicate commands to the implant 10, 14 once it has been implanted in the patient. A user interface, such as a personal computer (PC), laptop, or hand-held computer, may be used to enable communication with the implant, control the action (e.g., movement) of the implant, and provide feedback to the surgeon as to the action being performed.

The implant 10, 14 may be configured to include any necessary hardware and software to perform the desired functions. For example, the implant 10, 14 may be configured with a number of actuators, sensors, and other mechanisms to perform and measure an action and provide feedback to the user (e.g., the surgeon). The implant 10, 14 may also include the necessary hardware and software to facilitate the wireless communications link, along with any necessary or desired signal processing and analysis. The implant 10, 14 may also be embodied with a power source to power the actuators, sensors, and electronics. As will be discussed in greater detail below, energy to operate the actuators (or other devices) may also be externally provided to the implant (e.g., transcutaneously). In combination, the implant 10, 14 may be embodied with a sensor feedback scheme which facilitates external actuation thereof. For example, the implant 10, 14 may be actuated by a transcutaneous source, with the control of such a source utilizing input from a sensor associated with the implant 10, 14. In such a configuration, the sensor may be used to identify the need for actuation. During such actuation, the sensor provides feedback to monitor the implant's movement.

Numerous types of actuators may be used to facilitate movement of the implant 10, 14. For example, the implant 10, 14 may be embodied with one or more stepper motors, drive motors, servomotors, piezoelectric actuators, shape memory alloy actuators, paraffin actuators, linear piezoelectric motors, electromagnetic solenoids, electroactive polymers, or the like, to drive the movable components of the implant 10, 14. Such devices may be driven by a spring bias, fluid pressure, gas pressure, electric current, heat (e.g., nitinol or other shape memory alloy changing shape as a function of temperature change), or other types of energy.

Hence, it should be appreciated that an adjustable remote-controllable orthopaedic implant may be designed such that the implant can be actuated via transcutaneous energy transfer and/or an onboard power source so that the implant's shape, size, offset, alignment, length, etcetera can be adjusted. Multiple actuators may be utilized. A sensor (or multiple sensors) may be used to provide real-time feedback to the surgeon. Such feedback may be provided to the surgeon via any type of human machine interface. This feedback may be used to facilitate adjustment of the implant to a desired orientation/position.

One specific illustrative embodiment of an implant constructed with the concepts described herein is a joint space narrowing measurement device. Such a joint space narrowing measurement device may be used to monitor the distance between two bones (including any implants placed in them). Such a device may also be used to monitor the relative three-dimensional position and orientation of one implant component (e.g., the tibial component of a knee prosthesis) with respect to another implant component (e.g., the femoral component of a knee prosthesis). As the joint space narrows, the device enables a surgeon to identify the narrowing profile (e.g., medial or lateral dominant or a precise relative position and orientation of one component with respect to another indicating levels of subsidence, migration, fixation integrity, and potentially micromotion). An actuator, such as one of the actuators described above as well as a magnet driven actuator, may be included in either joint replacement component (e.g. in the knee, the tibial or femoral component). As the surgeon identifies the narrowing profile during a routine post-operative office visit, he or she may also choose to adjust the alignment/laxity of the components using the transcutaneously energized actuator. As noted above, the actuator(s) may be energized by an onboard power source as well. During such adjustment, the joint space narrowing measurement device can be used to provide real-time feedback of the adjustment. This will improve the adjustment and increase the likelihood that the proper adjustment is made.

Another specific exemplary embodiment of an implant constructed with the concepts described herein is a responsive orthopaedic implant in which an on-board sensor (or multiple sensors) and an on-board actuator (or multiple actuators) are used in combination. In such a case, the sensor monitors some physical, chemical, or other parameter(s). When the sensor detects some absolute or relative change in such a parameter (s), the orthopaedic implant responds by initiating some desirable adjustment through actuation of the on-board actuator. During such actuation, the sensor may continue to monitor the parameter(s). Actuation is terminated when the sensor detects that the parameter(s) has returned to within predetermined limits.

Figure 7:
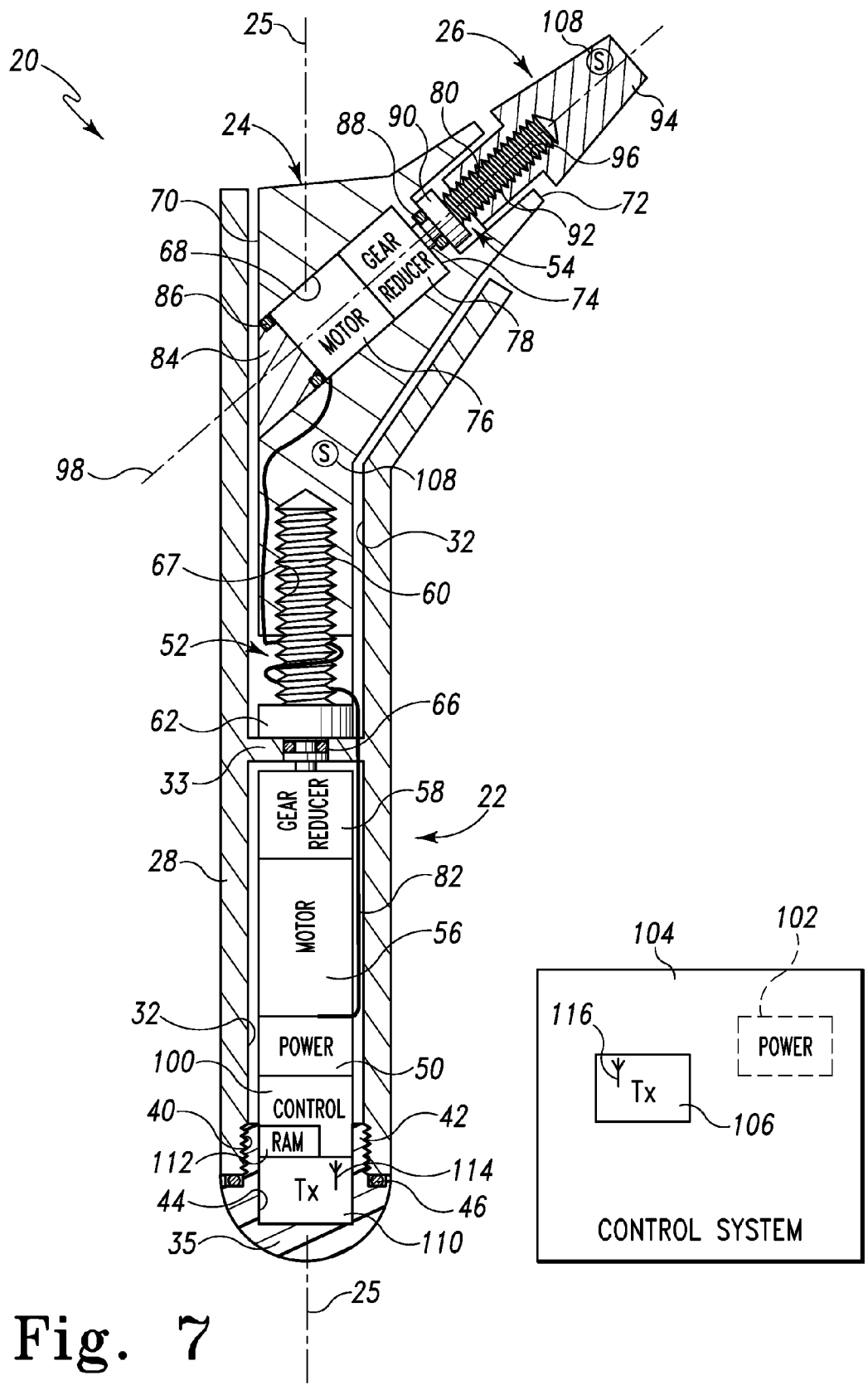
FIG. 7 is a cross-sectional view of an adjustable femoral prosthesis.

Referring now to FIG. 7, there is shown an adjustable femoral prosthesis 20 for implantation into a patient's femur during performance of a hip replacement procedure. It should be appreciated that although the concepts of the present disclosure are herein exemplarily described in regard to a prosthesis for use in the performance of a hip replacement procedure, the concepts of the present disclosure may be utilized in regard to a prosthesis for implantation into other bones of the body. For example, the concepts of the present disclosure may be utilized in the construction of a prosthesis for implantation into the humerus, radius, ulna, tibia, fibula, femur, glenoid, talus, spine, or any of the metatarsals or metacarpals.

The femoral prosthesis 20 includes a stem assembly 22, a body assembly 24 movable relative to the stem assembly 22, and a neck 26 movable relative to the body assembly 24. The neck 26 extends outwardly from the body assembly 24. A generally spherically shaped prosthesis (not shown) that mimics a natural femoral head may be taper fit or otherwise secured to the neck 26. The prosthesis 20 is configured to be implanted into the femur of a patient in order to replace certain natural features of the patient's femur as a result of, for example, disease or trauma. The prosthesis 20 is implanted into a surgically prepared (e.g., reamed and/or broached) medullary canal of the femur.

The stem assembly 22 and the body assembly 24 of the prosthesis 20 may be utilized to secure the patient's femur for movement relative to the patient's pelvis. In particular, the spherically shaped prosthesis secured to the neck 26 is positioned to bear on either the patient's natural acetabulum or a prosthetic socket in the form of a prosthetic cup (not shown) which has been implanted into the patient's pelvis to replace his or her acetabulum. In such a manner, the prosthesis 20 and the natural or artificial acetabulum collectively function as a system which replaces the natural "ball and socket" joint of the patient's hip.

Each of the stem assembly 22, the body assembly 24, and the neck 26 may be made of materials conventionally utilized in the construction of prosthetic implants. For example, the stem assembly 22, the body assembly 24, and the neck 26 may be constructed from implantable metals such as stainless steel, cobalt chrome, or titanium, including alloys of such metals. The stem assembly 22, the body assembly 24, and the neck 26 may also be constructed with non-metallic materials such as implant-grade polymers or ceramics.

The stem assembly 22 may be embodied in a number of different configurations in order to fit the needs of a given patient's anatomy and provide a variety of geometries and sizes. In particular, the stem assembly 22 may be configured in various different lengths to conform to the patient's anatomy (e.g., a relatively long stem assembly 22 for use with a long femur, a relatively short stem assembly 22 for use with a short femur, etcetera). Moreover, the stem assembly 22 may also be embodied in a bow-shaped configuration if required by a given patient's anatomy. Yet further, the stem assembly 22 may also be embodied in various diameters as required by a given patient's anatomy.

The stem assembly 22 is implanted into an elongated bore surgically formed in the patient's femur. As such, the stem assembly 22 may be constructed with materials which promote bone ingrowth into the outer surfaces of the stem assembly 22. Moreover, since bone cement may be used to secure the stem assembly 22 in the femur, the materials from which the stem assembly 22 is constructed may also be selected to promote interdigitation of bone cement into the outer surfaces of the stem assembly 22.

As shown in FIG. 7, the stem assembly 22 includes an outer shell 28 defining an elongated bore 32 therein. Illustratively, the bore 32 extends from a proximal end of the stem assembly 22 to a distal end of the stem assembly 22 to form a passageway therethrough. As is discussed in greater detail below, a portion of the body assembly 24 is received within the bore 32 for up and down movement along a longitudinal axis 25 which extends the length of the stem assembly 22 relative to the outer shell of the stem assembly 22 to adjust an overall length of the prosthesis 20. The body assembly 24, therefore is telescopically adjustable relative to the stem assembly 22. The distal end of the body assembly 22 is positioned in the elongated bore 32, whereas the proximal end of the body assembly 22 extends out of the bore 32. Illustratively, a proximal end of the bore 32 defines a larger diameter than a distal end of the bore 32. Further, an inner rim 33 of the outer shell 28 extends inwardly into the bore 32 to define a lower, distal cavity and an upper, proximal cavity.

The stem assembly 22 further includes an end cap 35 coupled to the distal end of the outer shell 28. Illustratively, the distal end of the bore 32 includes an inner threaded portion 40 and the end cap 35 includes a threaded portion 42 received within the distal end of the bore 32 of the outer shell 28. The end cap 35 further includes an inner bore 44 which communicates with the distal end of the bore 32 of the outer shell 28 to define the lower, distal cavity of the prosthesis 20. The end cap 35 may be made from a polymer such as ultra high molecular weight polyethylene. Illustratively, an o-ring seal 46 is positioned between the end cap 35 and the distal end of the outer shell 28 within a channel formed in the end cap 35 to prevent bodily fluids from entering the bore 32.

The prosthesis 20 further includes a power source 50, a first drive assembly 52 electrically coupled to and driven by the on-board power source 50, and a second drive assembly 54 also electrically coupled to and driven by the on-board power source. Illustratively, the first drive assembly 52 is coupled to both the stem assembly 22 and the body assembly 24 to move the body assembly 24 relative to the stem assembly 22 along the first axis 25 to increase and/or decrease an overall length of the prosthesis 20. The second drive assembly 54 is coupled to both the body assembly 24 and the neck 26 to move the neck 26 relative to the body assembly 24 to increase and/or decrease an overall offset and length of the prosthesis 20. Illustratively, the neck 26 is movable linearly along a second axis 98 extending along a length of the neck 26, as shown in FIG. 7, for example.

As shown in FIG. 7, the power source 50 is positioned within the distal end of the bore 32. A portion of the first drive assembly 52 is also positioned within the distal end of the bore 32, with another portion of the first drive assembly 52 being positioned within the proximal end of the bore 32.

The internal or on-board power source 50 of the prosthesis 20 may be embodied in numerous forms. For example, the power source 50 may be an on-board battery, such as a lithium iodine cell available from Wilson Greatbatch Technologies, Inc. (Clarence, N.Y.). Alternatively, the internal power source 50 of the prosthesis 20 may be an inductive power source such as a ferrite-loaded coil. A suitable ferrite-loaded coil is a small wound coil such as that available commercially from Predan SA (Kamanillas, Malaga, Spain). The configuration of such a wound coil may be based on the design and the selection of the electronic components of the prosthesis. For example, the power, frequency, and size of the coil may be selected to suit the other components of the prosthesis. Alternatively, a suitable ferrite-loaded coil may be wound using standard equipment such as that available from Aumann North America, Inc. (Fort Wayne, Ind.). When the coil is passed through an externally generated electromagnetic field, an electric current is formed through the coil which may be used to power the other components within the prosthesis 20. Other suitable power sources or power generators may be used as well.

For embodiments where the power source 50 includes an inductor, an external power source 102 may be provided at the point of care. In an illustrative embodiment, the external power source 102 may form a component of an external control system 104, and may include a coil that generates a localized electromagnetic field that acts upon the implanted ferrite coil to thereby supply power to the implanted electronics. Suitable external coils are commercially available from Predan SA (Kamanillas, Malaga, Spain). Generally, since the coils are likely to be used in close proximity to the patient, it may be desirable to select or design a coil that will not irritate or excessively heat the patient's skin and that can be easily handled by the operator or medical technician. The coil supplies a field at the desired frequency to stimulate the implanted power coil. Illustratively, the external control system 104 may also include a remote receiver or transceiver 106 to receive an output signal from any sensor 108 which may be positioned on or within the prosthesis 20. An internal transmitter or transceiver 110 associated with the controller 100 of the prosthesis 20 may then operate to transmit the sensor's signal to the external control system 104. As is discussed below, the external control system 104 may include other components as well.

Referring again to FIG. 7, the first drive assembly 52 includes a motor 56, a gear reducer 58 coupled to the motor 56, and a threaded drive shaft 60 coupled to the gear reducer 58. It is also within the scope of this disclosure for the first drive assembly 52 to include only the motor 56 and the drive shaft 60. In such an embodiment, the drive shaft 60 may then be coupled directly to the motor 56. As mentioned above, the power source 50 is coupled to and powers the motor 56 of the first drive assembly 52.

Illustratively, the motor 56 may be a DC stepper motor, a DC motor, or a rotary piezoelectric motor which has a rotational output. Suitable motors sized to fit within a prosthesis, such as the prosthesis 20, include, for example, those sold by MicroMo Electronics, Inc (Clearwater, Fla.), Sanyo (Bensenville, Ill.), and/or Aeroflex, Motion Control Products Division (Hauppauge, N.Y.). The gear reducer 58 includes an input shaft (not shown) coupled to the output shaft (not shown) of the motor 56, a system of gears (not shown), and an output shaft (not shown) coupled to the threaded drive shaft 60 to rotate the threaded shaft 60 in both an advancing direction and a retracting direction. The gears within the gear reducer 58 operate to reduce the rotational speed of the output shaft of the gear reducer 58 as compared to that of the output shaft of the motor 56.

Illustratively, as shown in FIG. 7, a base 62 of the threaded drive shaft 60 is coupled to the gear reducer 58. The base 62 includes a narrow, neck portion formed to receive a seal, such as an o-ring seal 66, therein. Illustratively, the outer shell 28 of the prosthesis 20 includes an inwardly extending rib 33 generally aligned with the neck of the base 62 of the threaded drive shaft 60.

The threaded end of the threaded drive shaft 60 is received within a threaded bore 67 formed in a distal end of the body assembly 24 of the prosthesis 20. As is described in greater detail below, the motor 56 drives the gear reducer 58 to cause the threaded drive shaft 60 to rotate. Due to the non-circular shape of the proximal end of the outer shell 28 and of the body assembly 24 received within the outer shell 28, the body assembly 24 is prevented from rotating with the threaded drive shaft 60 relative to the outer shell 28. Therefore, the rotational motion of the drive shaft 60 is translated to a linear up and down motion of the body assembly 24 relative to the stem assembly 22. For example, when the motor 56 is driven in a first direction, the body assembly 24 moves upwardly relative to the stem assembly 22 to increase an overall length of the prosthesis 20. However, driving the motor 56 in a second direction opposite from the first direction causes the body assembly 24 to move downwardly relative to the stem assembly 22 to decrease an overall length of the prosthesis 20. As is discussed in greater detail below, a controller 100 is coupled to the power source 50 and the motor 56 to control the power source 50 and the motor 56 in order to allow the surgeon or technician to adjust the overall length of the prosthesis 20 incrementally in a controlled manner.

As mentioned above, the body assembly 24 of the prosthesis 20 is positioned within the bore 32 of the stem assembly 22 and is located at a generally proximal end of the stem assembly 22. Further as mentioned above, the body assembly 24 includes the threaded bore 67 formed to receive the threaded drive shaft 60 of the first drive assembly 52 therein. The threaded bore 67 is formed in a distal end of the body assembly 24. A second bore 68 is formed in a proximal end of the body assembly 24. The second bore 68 extends from a rear surface 70 of the body assembly 24 to a top, neck surface 72 of the body assembly 24 and is formed to define a first compartment in communication with the rear surface 70 and a second compartment in communication with the top surface 72. Illustratively, an annular rib 74 of the body assembly 24 extends into the second bore 68 to define the first and second compartments.

The second drive assembly 54 is positioned within the second bore 68 and includes a motor 76, a gear reducer 78 coupled to the motor 76, and a threaded drive shaft 80 coupled to the gear reducer 78. As with the first drive assembly 52, the motor 76 of the second drive assembly 54 may be a DC stepper motor, a DC motor, or a rotary piezoelectric motor. Illustratively, the motor 76 is coupled to and in electrical communication with the power source 50 via an electrical cable 82 extending from the power source 50 to the motor 76 of the second drive assembly 54.

Illustratively, a plug 84 of the body assembly 24 is received within the first compartment of the bore 68, and an o-ring seal 86 is provided to seal the bore 68 and prevent bodily fluids from entering the bore 68. The plug 84 may be made from a polymer such as UHMWPE, for example. An o-ring seal 88 is also provided between the gear reducer 78 and the threaded drive shaft 80.

A base 90 of the threaded drive shaft 80 of the second drive assembly 54 is coupled to the gear reducer 78. An output shaft (not shown) of the motor 76 causes both an input and an output shaft (not shown) of the gear reducer 78 to rotate, which in turn causes the threaded drive shaft 80 to rotate.

The neck 26 of the prosthesis 20 includes a stem 92 received within the second compartment of the bore 68 of the body assembly 24. A tapered end 94 of the neck is coupled to the stem 92. The stem 92 includes a threaded bore 96. The threaded drive shaft 80 of the second drive assembly 54 is received within the threaded bore 96. While the motor 76 and gear reducer 78 cause the threaded drive shaft 80 to rotate, the neck 26 is prevented from rotating with the threaded drive shaft 80 by a keyed relationship between the neck 26 and the body assembly 24. For example, a groove (not shown) may be formed in the stem 92 of the neck 26 and a corresponding pin (not shown) may be protruding from an inside surface of the second compartment of the bore 68 formed in the body assembly 24. As such, the pin of the body assembly 24 may be received within the groove of the neck 26 to operate as an anti-rotation feature to prevent the neck 26 from rotating with the threaded screw drive 80 of the body assembly while allowing the neck 26 to linearly translate along the axis 98. It is also within the scope of this disclosure for the neck 26 to include a pin or key and the body assembly 24 to include a corresponding groove for receiving such a pin or key therein. It is further within the scope of this disclosure to provide an anti-rotation feature between the neck 26 and body assembly 24 by forming the stem 92 of the neck 26 and the proximal end of the body assembly 24 in a non-circular or non-round shape (such as, for example, oval, rectangular, or D-shaped) to prevent the neck 26 from rotating with the threaded drive shaft 80 relative to the body assembly 24.

Rotational movement of the drive shaft 80 and the threaded relationship between the drive shaft 80 and the neck 26 causes the neck 26 to move linearly along the second axis 98, shown in FIG. 7, relative to the body assembly 24. For example, when the motor 76 is driven in a first direction, the neck 26 moves outwardly along the second axis 98 in an extending direction away from the body assembly 24 to increase both the offset and the length of the prosthesis 20. However, driving the motor 76 in a second direction opposite the first direction causes the neck 26 to translate along the axis 98 in a retracting direction generally toward the body assembly 24 to decrease both the offset and the length of the neck 26 relative to the body assembly 24.

A surgeon or other technician may adjust the length and/or offset of the prosthesis 20 through remote control using a wireless communications link. For example, the external control system 104 may include a user interface, such as a laptop or PC, hand-held personal computer, personal data assistant, or any custom-designed data acquisition device, for example, having a wireless link for communication with the controller 100 of the prosthesis 20. The controller 100 may be embodied as any type of electronic controller such as, for example, general purpose micro-controllers, microprocessors, or application specific integrated circuits (ASICs). Moreover, the controller 100 may further include a receiver, transmitter, or transceiver 110 and a memory device 112 such as a random access memory (RAM) device. The controller 100 is configured with the appropriate hardware, software, and/or firmware to be responsive to the user commands received via the external control system 104.

The controller 100 of the prosthesis 20 is configured to communicate with the external control system 104 by use of the transceiver 110. The communication link between the controller 100 and the external control system 104 may use any type of suitable communication technology, such as radio frequency (RF) or an acoustic link. In some embodiments, the controller 100 transmits data received from the sensor 108 to the external control system 104. In the case of, for example, a position sensor, the controller transmits data indicative of the relative position of one or more of the components of the prosthesis (e.g., the stem assembly, the body assembly, or the neck). The external control system 104 may then display such data to the surgeon via a display device (not shown) such as a monitor or the like associated with the system's user interface. Armed with this information, the surgeon may then adjust the prosthesis 20. For example, the external control system 104 may communicate with the controller 100 to, for example, adjust the length and/or the offset of the prosthesis 20. For instance, the external control system 104 may transmit signals to the controller 100 which cause the controller 100 to operate the motors 56, 76 of the respective drive assemblies 52, 54 of the prosthesis 20.

As such, the surgeon may communicate with the controller 100 to instruct either motor 56, 76 of the respective drive assemblies 52, 54 to rotate in a first or second direction a particular number of rotations or for a particular length of time in order to control the adjustment of the prosthesis. For example, the surgeon may send a wireless signal to instruct either motor 56, 76 to rotate five revolutions in a particular direction, for example. Alternatively, the surgeon may simply enter a particular distance or select from a menu a particular distance, such as 5 mm, for example, as an amount by which the surgeon would like one or more of the components of the prosthesis 20 to be adjusted. Illustratively, the end cap 35 of the stem assembly 22 is made from a polymer material to allow RF or other signals to be transmitted therethrough.

As mentioned above, the prosthesis 20 may include a variety of onboard sensors gathering data and relaying that data back to the user interface of the external control system 104. For example, as described above, the prosthesis 20 may include one or more position sensors 108. The controller 100 of the prosthesis 20 may also include a modulator (not shown) to convert the output position signals of the position sensor 108 to an encoded signal that can be transmitted from the controller's transceiver 110 to a location outside the patient's body (e.g., the external control system 104). For example, the modulator can encode a particular position output signal into an RF wave by means of varying signal amplitude, frequency, or phase. The output from the modulator is transmitted outside of the patient's body by use of the transceiver's antenna 114. The external control system 104 demodulates and displays the data for the surgeon or other technician to read on the user interface. As such, the surgeon or other technician is provided with real-time feedback as to the position of the components of the prosthesis 20.

As mentioned above, the plastic end cap 35 of the prosthesis 20 allows signals to be transmitted from and received by the transceiver 110 within the prosthesis 20. Illustratively, the modulator may be positioned within the bore 32 of the stem assembly 22 and is electrically coupled to the power source 50. Suitable modulators are commercially available from Texas Instruments, Inc. (Dallas, Tex.) in the form of electronic chips. The modulator and transmitter may be provided as separate elements or may be provided as a single element capable of performing both these functions. In other words, the transmitter/transceiver may include a modulator or a modulating component. The modulator is also electrically coupled to and powered by the power source 50.

Looking again to FIG. 7, the transceiver 106 of the external control system 104 may include an antenna 116 (such as an RF antenna in the case of when RF technology is used) to receive signals from the antenna 114 of the prosthesis 20. The external control system 104 may be programmed to demodulate the RF signal transmitted from the antenna 114 of the prosthesis 20. The external control system 104 may be programmed to perform calculations necessary to convert the received and demodulated signal to the position sensed by the position sensor. As is discussed above, the external control system 104 may also be used to send instructions to the controller 100 of the prosthesis 20 to allow a surgeon or other technician to remotely operate the prosthesis 20. As such, the transceiver 106 of the external control system 104 may be operated to generate signals (e.g., RF signals) which are received by the antenna 114 of the prosthesis 20. Such signals may include commands regarding the control of one or both of the motors 56, 76 of each of the respective drive assemblies 52, 54 of the prosthesis 20, for example. As such, the controller 100 of the prosthesis 20 may include a demodulator (not shown) capable of demodulating and reading the signal as a set of instructions for operating motor 56 of the first drive assembly 52 and the motor 76 of the second drive assembly 54. For example, as mentioned above, a user may type a set of instructions into the user interface device of the external control system 104, thereby operating the motor 56 of the first drive assembly 52 to rotate a predetermined number of rotations (e.g., five rotations). This instruction signal is then sent from the external control system 104 to the prosthesis 20 to cause the motor to rotate as instructed to then cause the body assembly 24 to translate a certain distance, such as 5 mm, for example.

Figure 8:
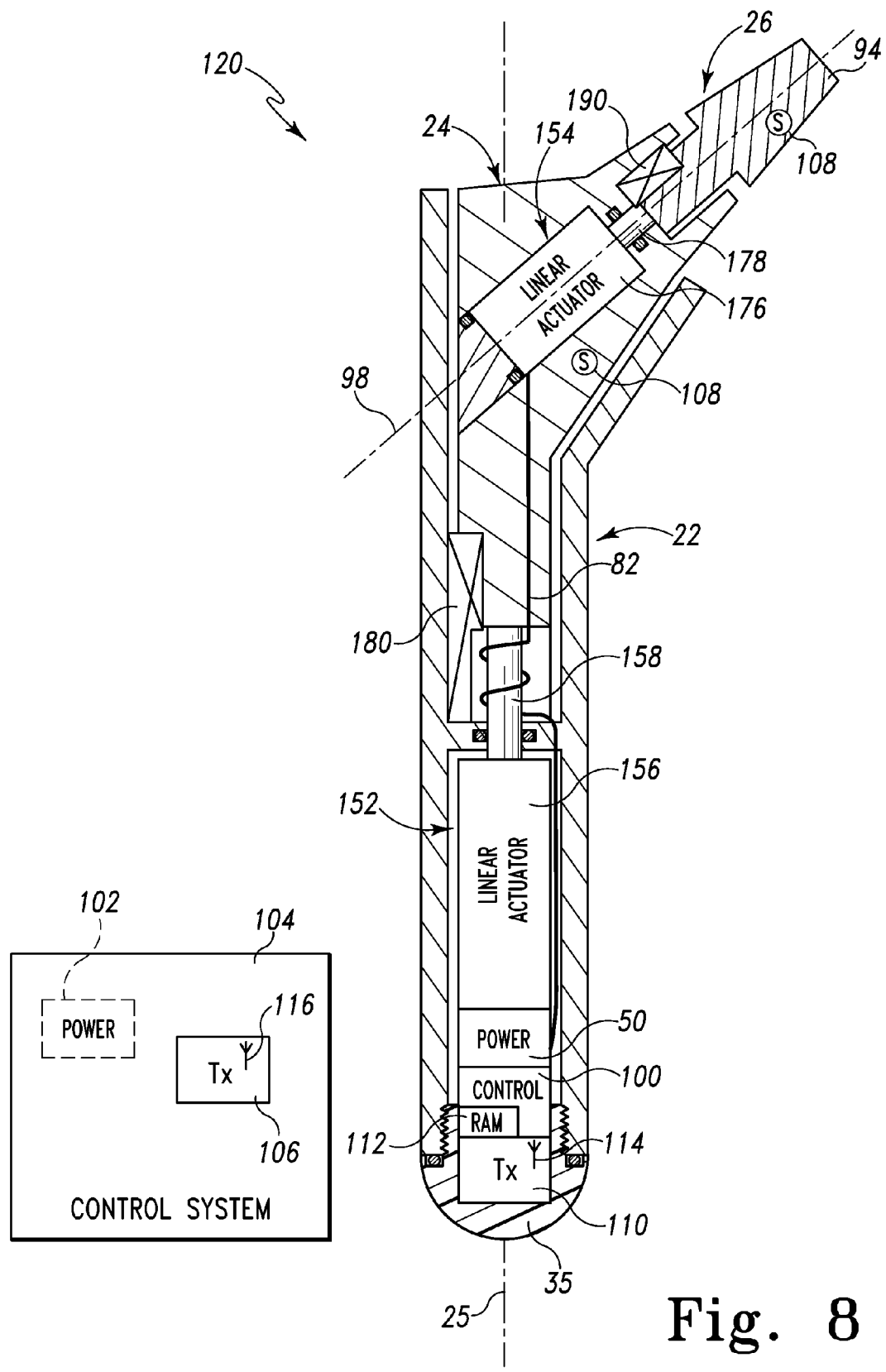
FIG. 8 is a cross-sectional view of another adjustable femoral prosthesis.

A second prosthesis 120 is shown in FIG. 8. The prosthesis 120 is similar to the prosthesis 20 shown in FIG. 7 and described above. Therefore, like reference numerals are used for like components. Further, the external control and operation of the prosthesis 120 is the same as or similar to that described above with respect to the prosthesis 20. The prosthesis 120 includes a first drive assembly 152 for telescopically adjusting the body assembly 24 of the prosthesis 120 relative to the stem assembly 22 along the first axis 25, and a second drive assembly 154 for telescopically adjusting the neck 26 relative to the body assembly 24 along a second axis 98. Each drive assembly 152, 154 is powered by the power source 50.

The first drive assembly 152 includes a linear actuator 156 having a linearly moving output shaft 158 coupled to the body assembly 24 to linearly translate the body assembly 24 relative to the stem assembly 22. The linear actuator 156 is electrically coupled to the power source 50. Similarly, the second drive assembly 154 includes a linear actuator 176 electrically coupled to the power source 50 and having a linearly moving output shaft 178 coupled to the neck 26 to linearly translate the neck 26 relative to the body assembly 24. Each of the linear actuators 156, 176 may include a piezoelectric actuator such as, for example, one sold by APC International, Ltd. (Mackeyville, Pa.) and/or by Piezosystem Jena, Inc. (Hopedale, Mass.), a shape memory alloy actuator such as, for example, one sold by NanoMuscle, Inc. (Antioch, Calif.), a paraffin actuator such as, for example, one sold by Stansys Research Corporation (Boulder, Colo.), a linear servomotor such as, for example, one sold by Anorad Rockwell Automation (Shirley, N.Y.) and/or Nippon Pulse America, Inc. (Radford, Va.), a linear piezomotor such as, for example, one sold by Nanomotion, Inc. (Ronkonkoma, N.Y.), an electromagnetic solenoid, or a non-commutated DC linear actuator such as, for example, one sold by H2W Technologies, Inc. (Valencia, Calif.). Other suitable linear actuators may be used as well. For example, a suitable linear actuator may include a linear actuator capable of producing enough force to move the body assembly relative to the stem assembly and to move the neck relative to the body assembly. Further, any suitable linear actuator includes those linear actuators sized to fit within a standard prosthesis, such as prosthesis 20, and/or any other type of prosthesis where movement of two portions relative to one another is desired. Additionally, other linear actuators may include linear actuators which provide actuator forces via bending or flexing movements such as, for example, an electroactive polymer (EAP) actuator.

The prosthesis 120 may also include a first locking mechanism 180, such as a ratchet, for example, to lock the relative position of the stem assembly 22 and the body assembly 24. The first locking mechanism 180 is shown diagrammatically in FIG. 8 and is coupled to both the stem assembly 22 and the body assembly 24 of the prosthesis 120. A second locking mechanism 190 of the prosthesis 120 may also be provided to lock the relative position of the neck 26 and the body assembly 24. The second locking mechanism 26 is also shown diagrammatically in FIG. 8 and is coupled to both the neck 26 and the body assembly 24 of the prosthesis 120. Suitable locking or ratchet mechanisms may include a friction ratchet or a toothed ratchet. It is also within the scope of this disclosure to provide a means for disengaging the first locking mechanism 180 from the body assembly 24, for example, and/or for disengaging the second locking mechanism 190 from the neck 26 in order to allow the body assembly 24 and the neck 26 to be retracted as well as extended. In operation, the ratchet or locking mechanisms 180, 190 generally carry some or all of the weight of the patient during a day to day loading or activity after the adjustment has been made. Various ratchet or locking mechanisms may include a friction ratchet for linear actuators having a smaller stroke such as piezoelectric drives, for example, and/or a toothed ratchet for use with linear actuators having a larger stroke such as shape memory alloys and paraffin actuators, for example. A solenoid may be used to disengage the ratchet or locking mechanism to allow the mechanism to move in the reverse direction to maintain the bidirectional movement of the various components of the prosthesis 120.

Implantation of the femoral prosthesis 20 will now be described in greater detail. Implantation of the femoral prosthesis 120 is the same as or similar to implantation of the prosthesis 20. As such, description pertaining to the prosthesis 20 only will be provided. Prior to implantation of the stem assembly 22, the patient's femur is surgically prepared. Specifically, the patient's femur is, for example, reamed and/or broached to form the bore in the medullary canal. Thereafter, the bore is filled, or partially filled, with bone cement. The bone cement may then be allowed to "set-up" for a period of time. Thereafter, the stem assembly 22 is implanted into the femur. Specifically, the distal tip of the stem assembly 22 is first advanced into the opening in the proximal end portion of the prepared femur and thereafter advanced down the medullary canal. The body assembly 24 of the prosthesis 20 extends out of the medullary canal of the femur.

In such a way, the femoral prosthesis 20 may be utilized to secure the patient's femur for movement relative to the patient's pelvis. In particular, when implanted in such a manner, the spherically-shaped prosthetic femoral head (not shown) secured to the neck 26 of the body assembly 24 is positioned to bear on either the patient's natural acetabulum or a prosthetic socket in the form of a prosthetic acetabular cup (not shown) which has been implanted into the patient's pelvis to replace his or her acetabulum. As a result, the femoral prosthesis 20 and the natural or artificial acetabulum collectively function as a system which replaces the natural "ball and socket" joint of the patient's hip.

Subsequent to implantation of the femoral prosthesis 20, it may become desirable to adjust the prosthesis 20. The prosthesis 20 may be adjusted along a number of different axes. For example, the prosthesis 20 may be adjust along a first axis to change the length of the prosthesis, and adjusted along a second axis to change the offset of the prosthesis.

To increase the length of the prosthesis 20, such as may be needed from time to time when the prosthesis 20 is implanted in a growing child, a wireless transmission of instructions may be sent to the prosthesis 20 from a point of care computer, as discussed above for example, to adjust the length and/or offset of the prosthesis 20. As mentioned above, the internal power source 50 powers the motors 56, 76 of the first and second drive assemblies 52, 54 which in turn rotate the respective threaded drive shaft 60, 80 to cause either axial movement of the body assembly 24 along axis 25 or to cause axial movement of the neck 26 along axis 98. Such extension of the body assembly 24 increases the length of the prosthesis 20, while extension of the neck 26 increases the both the offset and the length of the prosthesis 20. It should also be appreciated that the external control system 104 activates the respective motors 56, 76 to effectuate rotation of the threaded drive shafts 60, 80 transcutaneously thereby eliminating the need to surgically gain access to the prosthesis 20 to increase the length and/or offset thereof.

It should be appreciated that to decrease the length and/or offset of the prosthesis 20, such a command may be transmitted via an RF signal to the prosthesis 20 as well. Specifically, as mentioned above, a command to change or reverse the rotation of the output shaft of either motor 56, 76 causes the respective body assembly 24 and neck 26 to move in a retracting direction along their respective axes 25, 98. Such retraction of the body assembly 24 relative to the stem assembly 22 decreases the length of the prosthesis 20, while retraction of the neck 26 relative to the body assembly 24 decreases both the offset and the length of the prosthesis 20. It should also be appreciated that the external control system 104 activates the respective motors 56, 76 to effectuate rotation of the threaded drive shafts 60, 80 transcutaneously thereby eliminating the need to surgically gain access to the prosthesis 20 to decrease both the offset and the length thereof.

As described above, although the concepts of the present disclosure have herein been exemplarily described in regard to a prosthesis for use in the performance of a hip replacement procedure, the concepts of the present disclosure may be utilized in regard to other prostheses for use in other procedures. For example, the concepts of the present disclosure may be utilized in the construction of a hip prosthesis for implantation using minimally invasive techniques. These and other hip prostheses may be used in either primary or revision procedures. The concepts of the present disclosure may also be used in the construction of an adjustable tibial tray for use in a knee procedure. The concepts of the present disclosure may also be used in the construction of a spinal implant used to treat, amongst other things, scoliosis. The concepts of the present disclosure may also be used in the construction of fracture management devices thereby providing the device with the ability to compress a fracture site through external fixators, nails, and/or plates. The concepts of the present disclosure may also be used in the construction of expandable and contractible nails for use in, amongst other things, trauma procedures.

It should be appreciated that one or more miniature displacement sensors may be incorporated into the prostheses 20, 120. For example, the prostheses 20, 120 may be embodied with one or more Hall effect sensors, linear variable displacement transducers (LVDT's), differential variable reluctance transducers (DVRT's), reed switches, or the like. Such sensors may be incorporated into the femoral stem and neck of the adjustable prostheses 20, 120 and used to measure the distance extended between two components. For example, the sensors may be used to monitor the change in length of the stem and/or the neck in real-time while the prostheses 20, 120 is being adjusted. In a specific example, a Hall effect sensor may be used to monitor the position of the femoral stem and/or neck. During adjustment, the sensor may be used to provide real-time feedback. In addition to the prostheses 20, 120, such sensors and schemes may also be utilized in the construction of other types of prostheses.

It should also be appreciated that the output from a position sensor may be used to adjust the prostheses 20, 120 in response to a change in the position of the femoral component with respect to the femur in which it is implanted. For example, as the femoral component subsides and therefore changes its position with respect to the femur, the stem may be extended to compensate for the subsidence. The sensor, which may exemplarily be located on the moving shaft, continues to monitor its position with respect to the femur. When the sensor has reached a position with respect to the femur that is within predetermined limits, adjustment of the prostheses 20, 120 ceases. As with before, in addition to the prostheses 20, 120, such sensors and schemes may be utilized in the construction of other types of prostheses.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. An orthopaedic system comprising:
   an implantable hip prosthesis comprising:
   (i) a first component defining a first axis,
   (ii) a second component configured to receive a femoral head prosthesis and configured to move relative to the first component along a second axis extending oblique relative to the first axis,
   (iii) a drive assembly operable to adjust the position of the second component along the second axis relative to the first component,
   (iv) a sensor secured to one of the first component and the second component, the sensor being configured to sense the relative position of the first component and the second component, and
   (v) an electronic controller electrically coupled to the sensor so as to receive an output therefrom.

2. The orthopaedic system of claim 1, wherein the electronic controller is further configured to control operation of the drive assembly.

3. The orthopaedic system of claim 1, wherein the electronic controller comprises an antenna configured to receive signals from outside the body of a patient subsequent to the prosthesis being implanted in the body of a patient.

4. The orthopaedic system of claim 1, wherein the implantable hip prosthesis further comprises a power source electrically coupled to the drive assembly.

5. The orthopaedic system of claim 1, further comprising an external transmitter, wherein the external transmitter is configured to transmit signals from outside the body to the electronic controller subsequent to the prosthesis being implanted in the body of the patient.

6. An orthopaedic system comprising:
   an implantable hip prosthesis comprising:
   (i) an elongated stem assembly, the elongated stem assembly defining a first axis and configured to be received in a surgically prepared medullary canal of a femur,
   (ii) a neck configured to receive a femoral head prosthesis, the neck being configured to move along a second axis extending oblique to the first axis,
   (iii) a drive assembly operable to adjust the position of the neck along the second axis relative to the elongated stem assembly,
   (iv) a sensor configured to sense the relative position of the elongated stem assembly and the neck, and
   (v) an electronic controller electrically coupled to the sensor so as to receive an output therefrom.

7. The orthopaedic system of claim 6, wherein the electronic controller is further configured to control operation of the drive assembly.

8. The orthopaedic system of claim 6, wherein the electronic controller comprises an antenna configured to receive signals from outside the body of a patient subsequent to the prosthesis being implanted in the body of the patient.

9. The orthopaedic system of claim 6, wherein the implantable hip prosthesis further comprises a power source electrically coupled to the drive assembly.

10. The orthopaedic system of claim 6, further comprising an external transmitter, wherein the external transmitter is configured to transmit signals from outside the body of a patient to the electronic controller subsequent to the prosthesis being implanted in the body of the patient.

11. An orthopaedic implant, comprising:
an implantable hip prosthesis, comprising:
an elongated stem assembly,
a neck component,
a first drive assembly coupled to the elongated stem assembly and configured to move the elongated stem assembly along a first axis,
a second drive assembly coupled to the neck component and configured to move the neck component along a second axis, the second axis being different than the first axis, and
a power source secured to at least one of the elongated stem assembly and the neck component, wherein the power source is electrically coupled to both the first drive assembly and the second drive assembly.

12. The orthopaedic implant of claim 11, further comprising a controller secured to at least one of the elongated stem assembly and the neck component, wherein the controller is configured to control operation of both the first drive assembly and the second drive assembly.

13. The orthopaedic implant of claim 12, further comprising an external transmitter, wherein the external transmitter is configured to transmit signals from outside the body of a patient to the controller subsequent to the prosthesis being implanted in the body of the patient.

14. The orthopaedic implant of claim 13, further comprising an external receiver, wherein the external receiver is configured to receive signals generated by the controller from within the body subsequent to the prosthesis being implanted in the body of the patient.

15. The orthopaedic implant of claim 11, further comprising a position sensor configured to sense the position of at least one of the elongated stem assembly and the neck component.

* * * * *